United States Patent [19]

Miller et al.

[11] 4,167,575

[45] Sep. 11, 1979

[54] 3-ALKOXYISOTHIAZOLES

[75] Inventors: George A. Miller, Glenside; Sheldon N. Lewis, Willow Grove, both of Pa.

[73] Assignee: Rohm and Haas Company, Philadephia, Pa.

[21] Appl. No.: 819,086

[22] Filed: Jul. 26, 1977

Related U.S. Application Data

[62] Division of Ser. No. 659,814, Feb. 20, 1976, Pat. No. 4,053,479, which is a division of Ser. No. 855,048, Sep. 3, 1969, Pat. No. 3,957,808.

[51] Int. Cl.² ............... C07D 275/02; A61K 31/420
[52] U.S. Cl. .................................... 424/270; 548/213
[58] Field of Search ............... 260/306.8 A; 424/270

[56] References Cited

U.S. PATENT DOCUMENTS

| 2,871,243 | 1/1959 | Adams | 260/306.8 |
| 3,311,611 | 3/1967 | Lemieux | 260/302 |
| 3,476,765 | 11/1969 | Lemieux | 260/302 |
| 3,523,121 | 8/1970 | Lewis | 260/302 |

FOREIGN PATENT DOCUMENTS

| 1193050 | 5/1965 | Fed. Rep. of Germany | 260/302 |
| 6704241 | 9/1968 | Netherlands | 260/302 A |

OTHER PUBLICATIONS

Hatchard, J. Org. Chem., 29, pp. 660–665 (1964).

*Primary Examiner*—Donald G. Daus
*Assistant Examiner*—Lisa Jones

[57] ABSTRACT

Disclosed are certain novel 3-alkoxyisothiazoles. The 3-alkoxyisothiazoles and compositions containing them exhibit useful biocidal properties.

12 Claims, No Drawings

3-ALKOXYISOTHIAZOLES

This is a division of application Ser. No. 659,814, filed Feb. 20, 1976, now U.S. Pat. No. 4,053,479, which is a divisional of Ser. No. 855,048, filed Sept. 3, 1969, now U.S. Pat. No. 3,957,808.

This invention relates to novel 3-alkoxyisothiazoles (hereinafter referred to at times as "isothiazoles" or "alkoxyisothiazoles"), to biocidal compositions containing them, and to their utilization in the control of living organisms.

These novel 3-alkoxyisothiazoles can be represented by the formula

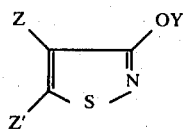

wherein
- Y is an alkyl group of 1 to 18 carbon atoms; a cycloalkyl group of 3 to 8 carbon atoms; an aralkyl group of up to 8 carbon atoms; a halogen-, lower alkyl-, or lower alkoxy-substituted aralkyl group of up to 10 carbon atoms; a carbalkoxyalkyl group of up to 12 carbon atoms; a dialkylaminoalkyl group of up to 12 carbon atoms; a haloalkyl group of up to 12 carbon atoms; an alkoxyalkyl group of up to 12 carbon atoms; an alkylthioalkyl group of up to 12 carbon atoms; an alkenyl group of up to 12 carbon atoms; or an alkynyl group of up to 12 carbon atoms;
- Z is hydrogen, halogen, a nitro group, a cyano group, a carboxy group, a carbalkoxy group of up to 8 carbon atoms, a carbamoyl group, an amino group, an aralkyl group of up to 8 carbon atoms, or a lower alkyl group; and
- Z' is hydrogen, halogen, an alkyl group of up to 8 carbon atoms, an aralkyl group of up to 8 carbon atoms, a lower alkylsulfinyl group, an aralkylsulfinyl group of up to 8 carbon atoms, a lower alkylsulfonyl group, an aralkylsulfonyl group of up to 8 carbon atoms, or an alkylamino group of up to 8 carbon atoms.

These 3-alkoxyisothiazoles can form novel salts with strong organic or inorganic acids. The salts also exhibit biocidal activity.

Where the expression "lower" is employed in conjunction with terms, such as for example, alkyl, alkylsulfinyl, alkylsulfonyl or haloalkyl, it is intended to indicate that the alkyl portion of the substituent group has a carbon content of 1 to 4 carbon atoms. Typically, the alkyl or alkyl portion may be methyl, ethyl, propyl, isopropyl, butyl, t-butyl, and the like.

Representative Y substituents include methyl, ethyl, propyl, isopropyl, butyl, hexyl, octyl, dodecyl, octadecyl, cyclohexyl, benzyl, 4-chlorobenzyl, trichlorobenzyl, carbethoxymethyl, carbethoxyethyl, diethylaminoethyl, diethylaminomethyl, chloroethyl, chloromethyl, bromomethyl, allyl, propargyl, methoxymethyl, 2-ethoxyethyl, methylthiomethyl, and 4-octynyl.

Representative Z substituents include hydrogen, methyl, ethyl, propyl, isopropyl, butyl, benzyl, chloro, bromo, iodo, cyano, carboxy, carbethoxy, carbamoyl, amino, and nitro.

Representative Z' substituents include hydrogen, methyl, ethyl, propyl, isopropyl, butyl, octyl, benzyl, chloro, bromo, methylsulfinyl, ethylsulfinyl, butylsulfinyl, benzylsulfinyl, methylsulfonyl, ethylsulfonyl, propylsulfonyl, benzylsulfonyl, ethylamino, and n-butylamino.

Typical compounds which fall within the scope of this invention include, for example,
3-methoxyisothiazole,
3-ethoxyisothiazole,
3-isopropoxyisothiazole,
3-n-hexyloxyisothiazole,
4-bromo-3-methoxyisothiazole,
4-iodo-3-methoxyisothiazole,
4-nitro-3-methoxyisothiazole,
4-cyano-3-methoxyisothiazole,
4-carbamoyl-3-methoxyisothiazole,
4-carboxy-3-methoxyisothiazole,
4-bromo-3-n-hexyloxyisothiazole,
3-n-dodecyloxyisothiazole,
3-benzyloxyisothiazolone,
3-trichlorobenzyloxyisothiazole,
3-carbethoxymethoxyisothiazole,
3-[2-(N,N-diethylamino)ethoxy]isothiazole,
3-(2-chloroethoxy)isothiazole,
3-allyloxyisothiazole,
3-(2-propynyloxy)isothiazole,
3-methoxymethoxyisothiazole,
5-chloro-3-methoxymethoxyisothiazole,
4-cyano-3-n-dodecyloxyisothiazole,
4-cyano-3-n-hexyloxyisothiazole,
3-n-propoxyisothiazole,
4-carboxy-3-n-dodecyloxyisothiazole,
3-n-butoxyisothiazole,
4-carboxy-3-n-butoxyisothiazole,
4-carboxy-3-n-hexyloxyisothiazole,
4-bromo-3-n-propoxyisothiazole,
4-cyano-3-n-propoxyisothiazole,
4-carbamoyl-3-n-propoxyisothiazole,
4-amino-3-n-propoxyisothiazole
4-chloro-3-methoxyisothiazole,
5-benzyl-3-methoxyisothiazole,
5-bromo-3-methoxyisothiazole,
5-chloro-3-methoxyisothiazole,
4,5-dichloro-3-methoxyisothiazole,
4,5-dibromo-3-methoxyisothiazole,
4-chloro-5-bromo-3-methoxyisothiazole,
4-bromo-5-chloro-3-methoxyisothiazole,
4-chloro-5-benzyl-3-methoxyisothiazole,
4-bromo-5-benzyl-3-methoxyisothiazole,
4-methyl-3-methoxyisothiazole,
4-ethyl-3-methoxyisothiazole,
4-butyl-3-methoxyisothiazole,
4-methyl-5-ethyl-3-methoxyisothiazole,
4,5-dimethyl-3-methoxyisothiazole,
4-methyl-5-chloro-3-methoxyisothiazole,
4-propyl-5-chloro-3-methoxyisothiazole,
4-butyl-5-chloro-3-methoxyisothiazole,
4-methyl-5-bromo-3-methoxyisothiazole,
4-ethyl-5-bromo-3-methoxyisothiazole,
4-ethyl-5-benzyl-3-methoxyisothiazole,
4-propyl-5-benzyl-3-methoxyisothiazole,
4-cyano-5-methylsulfinyl-3-methoxyisothiazole,
4-cyano-5-ethylsulfinyl-3-methoxyisothiazole,
4-cyano-5-benzylsulfinyl-3-methoxyisothiazole,
4-cyano-5-methylsulfonyl-3-methoxyisothiazole, 4-cyano-5-butylsulfonyl-3-methoxyisothiazole,
4-cyano-5-benzylsulfonyl-3-methoxyisothiazole,
4-carboxy-5-methylthio-3-methoxyisothiazole,
4-carbamoyl-5-methylthio-3-methoxyisothiazole,
4-cyano-5-n-butylamino-3-methoxyisothiazole,
4-cyano-5-ethylamino-3-methoxyisothiazole,
4-carbethoxy-3-methoxyisothiazole,
4-nitro-5-chloro-3-methoxyisothiazole, and
4-cyano-5-methyl-3-methoxyisothiazole.

The 3-alkoxyisothiazoles of the invention can be prepared by reacting with a halogenating agent a disulfide-imidate hydrochloride having the formula

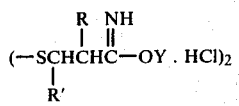

(II)

wherein R and R' are hydrogen, saturated alkyl groups, or araalkyl groups and Y is as defined above. Typical halogenating agents include chlorine, bromine, sulfuryl chloride, sulfuryl bromide, N-chlorosuccinimide, N-bromosuccinimide, iodine monochloride and the like. Chlorine and sulfuryl chloride are the preferred halogenating agents.

Temperature is not critical to the cyclization reaction process, and any desired temperature may be utilized. Generally and preferably the cyclization will be carried out in the range of about 0° to 60° C.

The reaction is generally carried out in an inert nonaqueous solvent, such as benzene, toluene, xylene, ethyl acetate, ethylene dichloride, 2-nitropropane, and the like.

The isothiazoles may be obtained as their isothiazolium salts during the cyclization process. Such salts have the following structure:

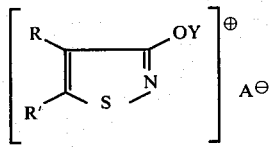

(III)

wherein Y, R, and R' are as defined above, and A is halogen. Where desired or necessitated, an acid acceptor can be incorporated in the reaction medium to avoid isothiazolium salt formation. Typical acceptors which can be utilized include t-amine bases, such as, for example, pyridine and triethylamine. It should be noted at this point that the isothiazolium salts can also be transformed or neutralized to free isothiazoles by being contacted with water or bases. Such procedures are, of course, well known to those skilled in the art.

To separate, if desired, the products prepared by the novel process of the invention from the reaction solution, any of the known techniques may be employed. Generally, separation will involve one or more of the steps of distillation, crystallization, filtration and the like.

For the cyclization of each mole of the disulfideimidate, three mole equivalents of the halogenating agent are required. When more than three mole equivalents of the halogenating agent are provided, the halogenation can occur at the 5-position and at both the 4- and 5-positions. Thus, when five mole equivalents of the halogenating agent are present, a 5-monohalogenated alkoxyisothiazole can be prepared, and when seven mole equivalents of the halogenating agent are present, a 4,5-dihalogenated alkoxyisothiazole can be obtained.

The 4-halo and 4,5-dihalo-3-alkoxyisothiazoles can also be prepared by halogenation of a 3-alkoxyisothiazole. Preparation of alkoxyisothiazoles having the 4- and 5-positions substituted with different halogen atoms is achieved by the halogenation of an isothiazolone already halogenated at one of the two positions in question. For example, a 4-bromo-5-chloro-3-alkoxyisothiazole can be obtained by bromination of a 5-chloro-3-alkoxyisothiazole. The starting isothiazole can, of course, be prepared by the cyclization of a disulfide-imidate as described herein.

The disulfide-imidates which are cyclized to form the 3-alkoxyisothiazoles are generally prepared from β,β'-dithiodipropionitriles which are in turn prepared from the reaction of acrylonitriles with ammonium tetrasulfide. The reaction of olefins with ammonium tetrasulfide to form disulfides is a reaction well known in the art. A β,β'-dithiodipropionitrile prepared from acrylonitriles in the manner stated above is then reacted with a suitable alcohol in the presence of hydrogen chloride to give the disulfide-imidate hydrochloride. The reaction is generally carried out in the presence of an inert non-aqueous solvent. The reaction can be run over a wide temperature range, with −20° C. to +100° C. being the preferred range.

Salts of the novel 3-alkoxyisothiazoles of the invention are also biocidally active. Preparation of the salts of these 3-alkoxyisothiazoles is readily achieved by reacting a 3-alkoxyisothiazole with a strong acid. The salts can be represented by Formula III, above, wherein A represents an anion of the strong acid. Typical strong acids include hydrobromic, nitric, sulfuric, perchloric, chlorosulfuric, chloroacetic, maleic, p-toluenesulfonic, hydrochloric, and the like. Separation of these salts from the reaction medium can be accomplished by any convenient means.

The 4-cyano, 4-carboxy, 4-carbalkoxy, 4-carbamoyl, 4-nitro, and 4-amino-3-alkoxyisothiazoles are all prepared by various classical reactions from the appropriate 3-alkoxyisothiazoles. A 4-bromo-3-alkoxyisothiazole, prepared as described above, is reacted with an equimolar or excess amount of cuprous cyanide, in a polar, non-hydroxylic solvent such as dimethylformamide, to give the 4-cyano-3-alkoxyisothiazole. The 4-carbamoyl-3-alkoxyisothiazoles are prepared by the hydrolysis of 4-cyano-3-alkoxyisothiazoles with sulfuric acid. When the carbamoyl derivative is hydrolyzed with nitrous acid, a 4-carboxy-3-alkoxyisothiazole is obtained. In the hydrolysis reactions, an equimolar amount or an excess of sulfuric acid or nitrous acid is used, and the reactions can be carried out in a wide variety of solvents. The 5-halo and 5-alkyl-4-carboxy and 4-carbamoyl-3-alkoxyisothiazoles are prepared from the corresponding 4-cyano-3-alkoxyisothiazole, which is in turn prepared from 3-alkoxyisothiazole.

The 4-nitro-3-alkoxyisothiazoles are prepared by a classical nitration of 3-alkoxyisothiazole in a nitric acid-sulfuric acid mixture, generally using an equimolar amount of nitric acid and excess sulfuric acid. The 4-amino-3-alkoxyisothiazoles can be prepared by reacting a 4-carbamoyl-3-alkoxyisothiazole with aqueous sodium hypobromite or sodium hypochlorite, the well-known Hofmann rearrangement.

The 3-alkoxyisothiazoles of this invention can also be prepared by alkylation of a 3-hydroxyisothiazole. This reaction can be represented as follows:

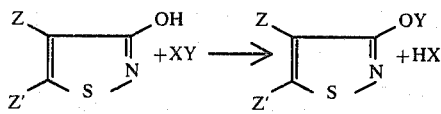

wherein Y, Z, and Z' are as defined above and X is a halogen, such as bromine, chlorine, or iodine. This reaction may also yield 3-isothiazolones having the formula

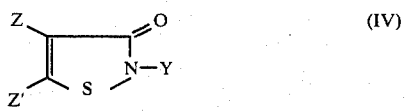

(IV)

wherein Y, Z, and Z' are as defined above, as well as the 3-alkoxyisothiazoles. Generally, an acid acceptor is used to facilitate the alkylation reaction. Among the suitable acid acceptors which can be used are inorganic bases, such as alkali and alkaline earth metal hydroxides, alcoholates, hydrides, amides, and carbonates, and organic bases, such as trialkylamines and pyridine. The ratio of the reactants—3-hydroxyisothiazole, alkylhalide, and acid acceptor—will usually be equimolar. However, an excess of any of the reactants can be used.

The alkylation reaction can be carried out in almost any solvent which will not interfere with the reaction, including water, alcohols, aliphatic and aromatic hydrocarbons, ethers, esters, amides, nitriles, and the like. The alkylhalide reagent itself can also be used as a solvent for the reaction. The alkylation reaction will proceed over a broad temperature range and temperature is not critical to the reaction. Generally, the alkylation will be carried out in the range of about 0° to 100° C.

The 3-hydroxyisothiazoles which are used as starting materials in the alkylation reaction can be prepared by several methods. 3-Hydroxyisothiazoles having the formula

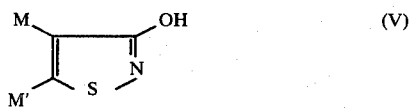

(V)

wherein M and M' are hydrogen, halogen, or saturated alkyl groups can be prepared by the cyclization of a disulfide-amide having the formula

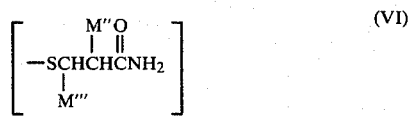

(VI)

wherein M'' and M''' are hydrogen or saturated alkyl groups. The cyclization is accomplished by reacting the disulfide-amide with a halogenating agent under conditions similar to the disulfideimidate cyclization described above. Halogenated 3-hydroxyisothiazoles can be prepared by a method similar to the halogenation of 3-alkoxyisothiazoles described above. The methods of W. D. Crow and N. J. Leonard, *J. Org. Chem.*, 30, 2660–2665 (1965), Goerdeler and Miller, *Chem. Ber.* 96, 944–954 (1963), and W. R. Hatchard, *J. Org. Chem.*, 28, 2163–2164 (1963), and an extension of the method of Goerdeler and Keuser, *Chem. Ber.*, 97, 3106 (1964), which involves the cyclization of a substituted α-cyanothiomalonamide with a halogenating agent, are also useful.

Among the 3-hydroxyisothiazoles which can be reacted with alkyl halides to produce the 3-alkoxyisothiazoles of the invention are:
3-hydroxyisothiazole,
4-bromo-3-hydroxyisothiazole,
4-chloro-3-hydroxyisothiazole,
5-benzyl-3-hydroxyisothiazole,
5-bromo-3-hydroxyisothiazole,
5-chloro-3-hydroxyisothiazole,
4,5-dichloro-3-hydroxyisothiazole,
4,5-dibromo-3-hydroxyisothiazole,
4-chloro-5-bromo-3-hydroxyisothiazole,
4-bromo-5-chloro-3-hydroxyisothiazole,
4-chloro-5-benzyl-3-hydroxyisothiazole,
4-bromo-5-benzyl-3-hydroxyisothiazole,
4-methyl-3-hydroxyisothiazole,
4-ethyl-3-hydroxyisothiazole,
4-butyl-3-hydroxyisothiazole,
4-methyl-5-ethyl-3-hydroxyisothiazole,
4,5-dimethyl-3-hydroxyisothiazole,
4-methyl-5-chloro-3-hydroxyisothiazole,
4-propyl-5-chloro-3-hydroxyisothiazole,
4-butyl-5-chloro-3-hydroxyisothiazole,
4-methyl-5-bromo-3-hydroxyisothiazole,
4-ethyl-5-bromo-3-hydroxyisothiazole,
4-ethyl-5-benzyl-3-hydroxyisothiazole,
4-propyl-5-benzyl-3-hydroxyisothiazole,
4-cyano-5-methylsulfinyl-3-hydroxyisothiazole,
4-cyano-5-ethylsulfinyl-3-hydroxyisothiazole,
4-cyano-5-benzylsulfinyl-3-hydroxyisothiazole,
4-cyano-5-methylsulfonyl-3-hydroxyisothiazole,
4-cyano-5-butylsulfonyl-3-hydroxyisothiazole,
4-cyano-5-benzylsulfonyl-3-hydroxyisothiazole,
4-carboxy-3-hydroxyisothiazole,
4-carbamoyl-3-hydroxyisothiazole,
4-nitro-3-hydroxyisothiazole,
4-carboxy-5-methylthio-3-hydroxyisothiazole,
4-carbamoyl-5-methylthio-3-hydroxyisothiazole,
4-cyano-5-n-butylamino-3-hydroxyisothiazole,
4-cyano-5-ethylamino-3-hydroxyisothiazole
4-iodo-3-hydroxyisothiazole,
4-cyano-3-hydroxyisothiazole,
4-carbethoxy-3-hydroxyisothiazole,
4-nitro-5-chloro-3-hydroxyisothiazole,
4-cyano-5-methyl-3-hydroxyisothiazole
5-methyl-3-hydroxyisothiazole,
4-bromo-5-methyl-3-hydroxyisothiazole,
4-cyano-5-methylthio-3-hydroxyisothiazole,
5-phenyl-3-hydroxyisothiazole,
4-carbamoyl-5-anilino-3-hydroxyisothiazole, and
4-cyano-5-anilino-3-hydroxyisothiazole.

By way of demonstration, the following examples are offered to illustrate this invention and are not to be construed as limitations thereof. Examples 1 to 30 are tabulated in Table I, which lists their formulas, elemental analyses, and melting points. Specific preparations of Examples 1, 6, 8, 13, 15, 16, 17, 18, 19, and 20 are set out below to illustrate the various methods of preparing the 3-alkoxyisothiazoles of the invention.

EXAMPLE 1

Preparation of 3-methoxyisothiazole

To a solution of 43 g. (0.25 mole) of β,β'-dithiodipropionitrile and 80 g. (2.5 mole) of methanol in 250 ml. of ethylene dichloride was added at 0°–5° C. 55 g. (1.5 mole) of anhydrous hydrogen chloride over 1 hour. The solution was then allowed to stand for several days at 5°–10° C., during which time dimethyl β,β'-dithiodipropionimidate dihydrochloride precipitated as a white solid. Filtration and drying gave 68 g. (88% of product.

To a suspension of 61.8 g. (0.2 mole) of dimethyl β,β'-dithiodipropionimidate dihydrochloride in 650 ml. of ethyl acetate at 25° C. was added over 1 hour 44.7 g. (0.63 mole) of chlorine. After chlorination, the reaction mixture was stirred for 1 hour, then filtered to give 44.4 g. of 3-methoxyisothiazole hydrochloride as a white solid. This material was dissolved in 100 ml. of water, neutralized with solid sodium bicarbonate and extracted thoroughly with ether. The ether extracts were dried over anhydrous magnesium sulfate and evaporated to give an oil residue which on distillation yielded 26.8 g. (58%) of 3-methoxyisothiazole, b.p. 147°–50° (760 mm).

EXAMPLE 6

Preparation of 3-dodecoxyisothiazole

To a slurry of 10.7 g. (0.25 mole) of sodium hydride (56% mineral oil dispersion) in 60 ml. of dimethylsulfoxide was added slowly at 25° C. a solution of 3-hydroxyisothiazole in 60 ml. of dimethylsulfoxide. Hydrogen gas was evolved vigorously and after addition 5.3 liters had been collected. To the resulting slurry was then added over 15 minutes 49.8 g. (0.2 mole) of 1-bromododecane. After stirring for 18 hours at 25° C., the reaction was heated to 80° C. for 1.5 hours. The reaction mixture was then diluted with 300 ml. of water and was extracted thoroughly with ether. The combined ether extracts were washed with water, dried over anhydrous magnesium sulfate, and evaporated to give an oil residue. This latter product on vacuum distillation gave 11.1 g. (21%) of 3-dodecoxyisothiazole, b.p. 142 (0.6 mm).

EXAMPLE 8

Preparation of 3-benzyloxyisothiazole

To a solution of 20.2 g. (0.2 mole) of 3-hydroxyisothiazole in 100 ml. of methanol was added 47.5 g. (0.22 mole) of 25% methanolic sodium methoxide solution, maintaining the temperature at 25°–30° C. To the resulting solution was then added dropwise at 25° C. 25.2 g. (9.2 mole) of benzyl chloride in 50 ml. of methanol. The reaction solution was then heated at reflux for 5 hours, during which time sodium chloride precipitated as a white solid. The resulting slurry was evaporated to an oil-solid mixture, which was slurried in ether and filtered. The ether solution was evaporated, and the oil residue was vacuum distilled to yield 18.7 g. (49%) of 3-benzyloxyisothiazole, b.p. 110° C. (0.3 mm).

EXAMPLE 13

Preparation of 3-allyloxyisothiazole

To a slurry of 10.7 g. (0.22 mole) of sodium hydride (56% mineral oil dispersion) in 60 ml. of dimethylformamide was added slowly at 25° C. 20.2 g. (0.2 mole) of 3-hydroxyisothiazole in 60 ml. of dimethylformamide. Hydrogen gas was evolved vigorously and at the completion of addition 5.2 liters had been collected. To the resulting solution was then added dropwise at 25° C. 24.2 g. (0.2 mole) of allyl bromide. After stirring at 25° C. for several hours, the reaction solution was diluted with water and extracted thoroughly with ether. The ether extracts were washed with water, dried over anhydrous magnesium sulfate, and evaporated to an oil residue. This latter material was vacuum distilled to give 7.3 g. (26%) of 3-allyloxyisothiazole, b.p. 60° (18 mm).

EXAMPLE 15

Preparation of 4-bromo-3-methoxyisothiazole

To a solution of 9.2 g. (0.08 mole) of 3-methoxyisothiazole in 20 ml. of glacial acetic acid was added dropwise at 25° C. a solution of 12.8 g. (0.08 mole) of bromine in 20 ml. of glacial acetic acid. After stirring overnight the slurry which had formed was poured into 400 g. of ice-water and allowed to stand. The precipitated solid was extracted into ether, and the aqueous phase was neutralized with solid sodium bicarbonate and extracted with ether again. The combined ether extract was dried over anhydrous magnesium sulfate and evaporated to leave an oil residue. This material was distilled to give 11.1 g. (72%) of 4-bromo-3-methoxyisothiazole, b.p. 70° C. (5 mm), which solidified on cooling in ice.

EXAMPLE 16

Preparation of 4-iodo-3-methoxyisothiazole

To a solution of 1.15 g. (0.01 mole) of 3-methoxyisothiazole in 5 ml. of glacial acetic acid was added dropwise over 10 minutes 1.80 g. (0.011 mole) of iodine monochloride. After standing for several days the reaction solution was poured onto ice to precipitate an oil, which on continued washing with water gave after filtering and drying 1.0 g. (42%) of 4-iodo-3-methoxyisothiazole as a tan solid. Crystallization from hexane gave this product as a white solid, m.p. 61°–63° C.

EXAMPLE 17

Preparation of 4-nitro-3-methoxyisothiazole

To a solution of 10 ml. of concentrated sulfuric acid and 2 g. (0.022 mole) of 70% nitric acid was added over several minutes 2.3 g. (0.02 mole) of 3-methoxyisothiazole. The temperature rose to 40° C. and was controlled at that point by cooling. After stirring for 5 hours the reaction solution was poured into 30 ml. of ice-water to precipitate 0.5 g. (16%) of 4-nitro-3-methoxyisothiazole as a white solid, m.p. 118°–122° C.

EXAMPLE 18

Preparation of 4-cyano-3-methoxyisothiazole

To a solution of 38.8 g. (0.2 mole) of 4-bromo-3-methoxyisothiazole prepared as in Example 15 in 80 ml. of dimethylformamide was added 54 g. (0.6 mole) of cuprous cyanide. The mixture was stirred and heated at reflux for 1 hour. Then the reaction mixture was cooled to 25° C., and 40 g. (0.81 mole) of sodium cyanide in 120 ml. of water was added in portions. The mixture exothermed to 60°–70° C. and was allowed again to cool to 25° C. The reaction solution was then extracted thoroughly with ether. The ether extracts were washed with 10% sodium cyanide solution and then water. After drying over anhydrous magnesium sulfate and evaporation 23.4 g. (83%) of 4-cyano-3-methoxyisothiazole was obtained as a white solid, m.p. 60°-62° C. after crystallization from ligroin (90°-120°).

EXAMPLE 19

Preparation of 4-carbamoyl-3-methoxyisothiazole

A solution of 2.8 g. (0.02 mole) of 4-cyano-3-methoxyisothiazole prepared as in Example 18 in 30 ml. of 75% sulfuric acid was heated at 70° C. for 0.5 hour. The solution was then cooled and poured into ice to give after filtration and drying 0.95 g. of 4-carbamoyl-3-methoxyisothiazole, m.p. 165°-168° C. By continuous ether extraction of the aqueous filtrate an addition 1.13 g. of 4-carbamoyl-3-methoxyisothiazole was obtained to give a total yield of 2.08 g. (66%).

EXAMPLE 20

Preparation of 4-carboxy-3-methoxyisothiazole

To a solution of 7.9 g. (0.05 mole) of 4-carbamoyl-3-methoxyisothiazole prepared as in Example 19 in 90 ml. of 80% sulfuric acid at 10°-15° C. was added slowly beneath the surface of the liquid a solution of 9.5 g. (0.137 mole) of sodium nitrite in 13 ml. of $H_2O$. When addition was complete the solution was allowed to come to 25° C., and then was heated to 60° C. for several minutes. After cooling to 25° C. the reaction solution was poured onto ice to precipitate 3.64 g. (46%) of 4-carboxy-3-methoxyisothiazole as a white solid, m.p. 182°-185° C.

including microorganisms. They are useful as bactericidal, algaecidal, fungicidal, and nematocidal agents, for example.

Antibacterial and antifungal activity were evaluated by the Serial Dilution Test (Broth Titor Test) wherein a series of broths containing varying dilutions of a test compound and an organism are halved starting with 1:1,000. The values obtained which are also shown in Table II represent the maximum dilution in parts per millions at which the compound under evaluation renders complete control of the organism. *Staphylococcus aureus* (*S. aureus*) and *Escherichia coli*, (*E. coli*) were the bacterial organisms employed in this test, and the fungi employed were *Aspergillus niger* (*A. niger*) and *Rhizopus stolonifer* (*R. stol.*).

TABLE II

MICROBIOLOGICAL ACTIVITY
(minimum microbistatic concentration, ppm)

| Example No. | Bacteria | | Fungi | |
|---|---|---|---|---|
| | S. aureus | E. coli. | A. niger | R. Stol. |
| 1 | >1000 | 1000 | >500 | >500 |
| 2 | 1000 | 1000 | 500 | 500 |
| 4 | 1000 | 500 | | |
| 5 | 250 | >1000 | 63 | 16 |
| 6 | 500 | 1000 | >500 | >500 |
| 7 | 125 | 125 | | |
| 8 | 250 | 250 | >500 | 500 |
| 9 | 500 | >1000 | 250 | 125 |
| 10 | 1000 | 1000 | >500 | >500 |
| 11 | 1000 | 500 | >500 | >500 |

TABLE I

3-Alkoxyisothiazole Examples

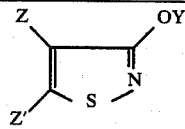

| Ex. No. | Z | Z' | b.p./m.p. | Y | Analysis** | | | | |
|---|---|---|---|---|---|---|---|---|---|
| | | | | | C | H | N | S | Halogen |
| 1 | H | H | 72° (52 mm) | $CH_3$ | 41.77(41.7) | 4.35(4.4) | 11.95(12.2) | 27.90(27.8) | |
| 2 | H | H | 36° (0.3 mm) | $C_3H_7$-n | 50.42(50.4) | 6.49(6.3) | 9.92(9.8) | 22.44(22.4) | |
| 3 | H | H | 95° (26 mm) | $CH(CH_3)_2$ | 50.56(50.4) | 6.49(6.3) | 9.80(9.8) | 22.05(22.4) | |
| 4 | H | H | 42° (0.1 mm) | $C_4H_9$-n | 54.06(53.5) | 7.21(7.0) | 8.76(8.9) | 20.24(20.4) | |
| 5 | H | H | 61° (0.4 mm) | $C_6H_{13}$-n | 58.59(58.4) | 7.98(8.1) | 7.51(7.6) | 17.18(17.3) | |
| 6 | H | H | 142° (0.6 mm) | $C_{12}H_{25}$-n | 68.39(66.9) | 9.90(10.0) | 4.82(4.7) | 11.72(11.9) | |
| 7 | H | H | 94° (0.5 mm) | $CH_2OCH_3$ | 41.14(41.1) | 5.42(5.5) | 9.70(9.6) | 22.07(21.9) | |
| 8 | H | H | 110° (0.3 mm) | $CH_2C_6H_5$ | 62.27(62.9) | 4.73(4.7) | 7.64(6.3) | 16.63(16.8) | |
| 9 | H | H | 66°-9°* | $CH_2C_6H_2Cl_3$ | 42.53(40.9) | 2.52(2.0) | 4.22(4.7) | 9.86(10.8) | Cl, 36.13 (36.1) |
| 10 | H | H | 94° (1.25 mm) | $CH_2CO_2C_2H_5$ | 45.54(44.9) | 5.05(4.8) | 6.94(7.5) | 16.70(17.1) | |
| 11 | H | H | 80° (0.1 mm) | $-C_2H_4N(C_2H_5)_2$ | 53.38(54.0) | 7.70(8.0) | 14.05(14.0) | 16.26(16.0) | |
| 12 | H | H | 56° (0.35 mm) | $-C_2H_5Cl$ | 38.07(36.9) | 4.32(3.7) | 7.79(8.6) | 19.26(19.63) | Cl, 21.67 (21.3) |
| 13 | H | H | 60° (18 mm) | $-CH_2CH=CH_2$ | 51.43(51.2) | 4.95(4.9) | 9.58(9.9) | 22.59(22.8) | |
| 14 | H | H | 65° (0.4 mm) | $-CH_2C\equiv CH$ | 51.37(51.7) | 3.98(3.6) | 9.75(10.1) | 23.01(23.0) | |
| 15 | Br | H | 70° (5 mm) | $CH_3$ | 24.82(24.7) | 2.18(2.1) | 7.20(7.2) | 16.21(16.5) | Br, 40.48 (41.2) |
| 16 | I | H | 61°-30°* | $CH_3$ | 19.43(19.9) | 1.50(1.7) | 5.51(5.8) | 13.32(13.3) | I, 52.15 (52.7) |
| 17 | $NO_2$ | H | 118°-22°* | $CH_3$ | 30.13(30.0) | 2.60(2.5) | 17.49(17.5) | 19.95(20.0) | |
| 18 | CN | H | 60°-2°* | $CH_3$ | 42.40(42.8) | 2.98(2.9) | 19.98(20.0) | 22.44(22.8) | |
| 19 | $CONH_2$ | H | 165°-68°* | $CH_3$ | 38.16(38.0) | 3.78(3.8) | 17.60(17.7) | 20.24(20.3) | |
| 20 | $CO_2H$ | H | 182°-5°* | $CH_3$ | 38.13(37.7) | 3.13(3.1) | 8.74(8.8) | 20.02(20.1) | |
| 21 | Br | H | 115° (0.3 mm) | $C_6H_{13}$-n | 41.26(40.9) | 5.47(5.3) | 5.21(5.3) | 12.01(12.12) | Br, 30.65 (30.3) |
| 22 | CN | H | 40°-2°* | $C_6H_{13}$-n | 56.83(57.1) | 6.51(6.7) | 13.18(13.3) | 15.13(15.2) | |
| 23 | $CO_2H$ | H | 78°-9°* | $C_6H_{13}$-n | 51.91(52.4) | 6.34(6.6) | 6.07(6.1) | 12.47(13.9) | |
| 24 | CN | H | 73°-5°* | $C_{12}H_{25}$-n | 65.04(65.3) | 8.72(8.8) | 9.38(9.5) | 10.72(10.9) | |
| 25 | $CO_2H$ | H | 87°-90°* | $C_{12}H_{25}$-n | 61.32(61.3) | 8.78(8.6) | 5.03(4.5) | 9.91(10.2) | |
| 26 | H | Cl | 46° (0.05 mm) | $CH_2OCH_3$ | 33.01(33.4) | 3.43(3.3) | 7.86(7.8) | 18.61(17.8) | Cl, 20–46 (19.2) |
| 27 | Br | H | 50° (0.05 mm) | $C_3H_7$-n | 33.13(32.4) | 3.79(3.6) | 6.08(6.3) | 14.14(14.4) | Br, 35.40 (36.0) |
| 28 | CN | H | 71° (0.025 mm) | $C_3H_7$-n | 50.02(50.0) | 5.19(4.8) | 16.34(16.7) | 19.28(19.1) | |
| 29 | $CONH_2$ | H | 97°-98°* | $C_3H_7$-n | 43.50(45.2) | 5.62(5.4) | 14.30(15.0) | 17.37(17.2) | |
| 30 | $NH_2$ | H | 149°-50°* | $C_3H_7$-n . HCl | 37.28(37.0) | 5.71(5.7) | 14.19(14.4) | 16.71(16.4) | 17.88 (18.2) |

*Melting Point
**The number parenthesized represents the theoretical value, as calculated, using the empirical formula of each compound.

The novel alkoxyisothiazoles and salts of this invention are biocidally active compounds, and as such, are suitable for the control of various living organisms,

| 12 | 1000 | 1000 | >500 | >500 |
| 13 | 1000 | 1000 | >500 | >500 |
| 14 | 1000 | 500 | >500 | 500 |

TABLE II-continued

| | MICROBIOLOGICAL ACTIVITY | | | |
|---|---|---|---|---|
| | (minimum microbistatic concentration, ppm) | | | |
| Example | Bacteria | | Fungi | |
| No. | S. aureus | E. coli | A. niger | R. Stol. |
| 15 | 1000 | 1000 | >500 | >500 |
| 16 | 1000 | 1000 | 250 | 250 |
| 18 | 1000 | 1000 | >500 | >500 |
| 19 | 500 | 1000 | >500 | >500 |
| 20 | >1000 | >1000 | | |
| 21 | 250 | >1000 | 500 | 31 |
| 22 | 63 | 1000 | 250 | 31 |
| 24 | 1000 | 1000 | | |
| 25 | 31 | >1000 | 500 | 250 |
| 26 | 250 | 250 | 250 | 125 |

3-Alkoxyisothiazoles were also evaluated as algaecides by the Fitzgerald Test (Applied Microbiology, 7, 205-211, No. 4, 1959).

The alkoxyisothiazoles can also be used in seed treatment applications. By seed treatment is meant the disseminating of a biocidally active material over a seed subject to the attack of microorganisms, and particularly fungi, in an amount which is effective to control such microorganisms without deleteriously effecting such seed. In most circumstances, the biocidally active material, in this case, the alkoxyisothiazoles or compositions containing them, will be applied to the surface area of the seeds to be treated. This may be accomplished by means common to the art, such as slurrying, socking, dusting, spraying and the like.

Evaluation of the alkoxyisothiazoles with regard to further pesticidal activity demonstrated their use as nematocides.

For the nematode test, soil was homogeneously inoculated with a macerated blend of tomato roots heavily knotted with the root-knot nematode. Ten ml. of a test solution of the 3-alkoxyisothiazole being evaluated was added to 200 ml. of the inoculated soil in a 16 oz. jar to give a concentration by volume of about 60, 30, or 15 ppm. The jar was then shaken to insure thorough mixing and kept capped for 72 hours. The soil was then placed into a 3-inch deep plastic plant pot and allowed to air for about 24 hours after which time 3 cucumber (*Cucumis sativus*) seeds were planted. About twenty-three days thereafter, the cucumber plants were removed from the soil and the root systems examined for the presence of knots. A total of 50 knots is considered as no control (−) and less than that as a measure of control.

TABLE III

| | NEMATOCIDAL ACTIVITY | | |
|---|---|---|---|
| Example | Number of Knots | | |
| No. | 60 ppm | 30 ppm | 15 ppm |
| 2 | 20 | — | |
| 4 | 0 | — | |
| 5 | 0 | 47 | |
| 8 | 0 | 21 | |
| 12 | 8 | 0 | 20 |
| 14 | 4 | | |
| 26 | 8 | | |
| Control | 50-100 | | |

Generally, control of a living organism is achieved in accordance with this invention by contacting the organism with an alkoxyisothiazole in an amount which is effective to control the organism. Any of the techniques known in the art can be employed to disseminate the alkoxyisothiazoles in a manner so as to achieve the desired contact with the organism to be controlled. Spraying and fumigating are typical of such techniques.

The compounds of this invention can be utilized as slimicides, algaecides, bactericides, fungicides or combinations thereof in any locus and particularly in aqueous media, such as water-cooling systems, swimming pools, paper pulp processes, water-based paints, and the like. In addition, these compounds and/or compositions containing them can function as preservatives, and especially fabric preservatives, soap additives, sanitizing agents, preservatives for metal working compounds, and the like.

In general, a locus subject to attack by microorganisms can be protected in accordance with this invention by incorporating into said locus an alkoxyisothiazole in an amount which is effective to control said microorganisms. The exact amount of alkoxyisothiazole required will, of course, vary with the medium being protected, the microorganisms being controlled, the particular alkoxyisothiazoles or compositions containing the alkoxyisothiazoles being employed and the like. Typically, in a liquid medium, excellent control is obtained when the alkoxyisothiazoles are incorporated in the range of 0.1 to 10,000 parts per million (ppm.) or 0.00001 to 1% based on the weight of the medium. A range of 1 to 2000 ppm. is preferred.

The term "control", as employed in the specification and claims of this application, is to be construed as the effect of any means which adversely affects the existence or growth of any living organism or microorganism. Such effect may comprise a complete killing action, eradication, arresting in growth, inhibition, reduction in number or any combination thereof.

The alkoxyisothiazoles can also be used as agricultural fungicides. As such, they are particularly valuable when formulated in a fungicidal composition. Such compositions normally comprise an agronomically acceptable carrier and the compounds disclosed herein as the active agent or agents. Where necessary or desirable, surfactants or other additives may be incorporated to give uniformly formulated mixtures. By "agronomically acceptable carrier" is meant any substance which can be utilized to dissolve, dispense or diffuse the chemical incorporated therein without impairing the effectiveness of the toxic agent and which does no permanent damage to such environment as soil, equipment and agronomic crops.

For use as pesticides, the compounds of this invention are usually taken up in an agronomically acceptable carrier or formulated so as to render them suitable for subsequent dissemination. For example, the alkoxyisothiazoles may be formulated as wettable powders, emulsion concentrates, dusts, granular formulations, aerosols or flowable emulsifiable concentrates. In such formulations, the alkoxyisothiazoles are extended with a liquid or solid carrier and, when desired, suitable surfactants are likewise incorporated.

Thus, compounds of this invention can be dissolved in a water-miscible liquid such as ethanol, isopropanol, acetone, and the like. Such solutions are easily extended with water.

The isothiazoles can be taken up on or mixed with a finely particled solid carrier, as for example, clays, inorganic silicates, carbonates, and silicas. Organic carriers may also be employed. Dust concentrates are commonly made wherein alkoxyisothiazoles are present in the range of 20 to 80%. For ultimate applications these concentrates are normally extended with additional solid from about 1 to 20%.

Wettable powder formulations are made by incorporating the compounds of this invention in an inert, finely divided solid carrier along with a surfactant which may be one or more emulsifying, wetting, dispersing or spreading agents or blend of these. The alkoxyisothiazoles are usually present in the range of 10 to 80% by weight and the surfactants in from 0.5 to 10% by weight. Commonly used emulsifying and wetting agents include polyoxyethylated derivatives of alkylphenols, fatty alcohols, fatty acids and alkylamines; alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the isothiazole toxicant onto the solid carrier by means of a volatile solvent, such as acetone. In this manner, adjuvants, such as activators, adhesives, plant nutrients, synergists and various surfactants, may also be incorporated.

Emulsifiable concentrate formulations may be prepared by dissolving the isothiazoles of this invention in an agronomically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents are commonly employed. The surfactants useful as emulsifying agents may constitute about 0.5 to 10% by weight of the emulsifiable concentrate and may be anionic, cationic or nonionic in character. Anionic surfactants include alcohol sulfates or sulfonates, alkylarene sulfonates and sulfosuccinates. Cationic surfactants include fatty acid alkyl amine salts and fatty acid alkyl quaternaries. Non-ionic emulsifying agents include ethylene oxide adducts of alkylphenols, fatty alcohols, mercaptans and fatty acids. The concentration of the active ingredients may vary from 10 to 80%, preferably in the range of 25 to 50%.

For use as phytopathogenic agents, these compounds should be applied in an effective amount sufficient to exert the desired biocidal activity by techniques well known in the art. Usually, this will involve the application of the alkoxyisothiazoles to the locus to be protected in an effective amount when incorporated in an agronomically acceptable carrier. However, in certain situations it may be desirable and advantageous to apply the compounds directly onto the locus to be protected without the benefit of any substantial amount of carrier. This is a particularly effective method when the physical nature of the alkoxyisothiazoles is such as to permit what is known as "low-volume" application, that is, when the compounds are in liquid form or highly soluble in higher boiling solvents, so that they can be dissolved therein at high concentrations.

The application rate will, of course, vary depending upon the purpose for such application, the alkoxyisothiazoles being utilized, the frequency of dissemination and the like.

For use as bactericides and fungicides, dilute sprays may be applied at concentrations of 0.05 to 20 pounds of the active alkoxyisothiazole ingredient per 100 gallons of spray. They are usually applied at 0.1 to 10 pounds per 100 gallons and preferably at 0.125 to 5 pounds per 100 gallons. In more concentrated sprays, the active ingredient is increased by a factor of 2 to 12. With dilute sprays, applications are usually made to the plants until run-off is achieved, whereas with more concentrated or low-volume sprays the materials are applied as mists.

The compounds of this invention can be utilized as the sole biocidal agents or they can be employed in conjunction with other fungicides, insecticides, nematocides, and other comparable pesticides.

It is to be understood that changes and variations may be made without departing from the spirit and scope of the invention as defined by the appended claims.

We claim:

1. A compound of the formula

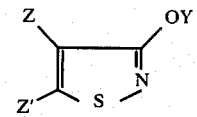

wherein

Y is an alkyl group of 1 to 18 carbon atoms; a cycloalkyl group of 3 to 8 carbon atoms; a benzyl group; a halogen-, ($C_1$–$C_4$)alkyl-, or ($C_1$–$C_4$)alkoxy-substituted benzyl group; a carbalkoxyalkyl group of up to 12 carbon atoms; a dialkylaminoalkyl group of up to 12 carbon atoms; a haloalkyl group of up to 12 carbon atoms; an alkoxyalkyl group of up to 12 carbon atoms; an alkylthio alkyl group of up to 12 carbon atoms; an alkenyl group of up to 12 carbon atoms; or an alkynyl group of up to 12 carbon atoms;

Z is a nitro group or an amino group;

Z' is hydrogen, halogen, or a ($C_1$–$C_4$)alkyl group; and the salts thereof with a strong acid.

2. A compound according to claim 1 wherein Z' is hydrogen.

3. A compound according to claim 1 wherein Y is an alkyl group of 1 to 18 carbon atoms.

4. A compound according to claim 1 wherein Y is a benzyl group.

5. An agricultural composition adapted to control microorganisms, bacteria, algae, fungi, and nematodes which comprises an agronomically acceptable carrier and a compound according to claim 1.

6. An agricultural composition according to claim 5 which comprises, in addition, a surfactant.

7. A method of controlling a microorganism, bacteria, algae, fungi, and nematode which comprises contacting with said organisms, in an amount which is effective to control said organisms, a compound according to claim 1.

8. A method according to claim 7 wherein said organism is a nematode.

9. A method for protecting a locus subject to the attack of microorganisms which comprises incorporating into said locus, in an amount which is effective to control said microorganisms, a compound according to claim 1.

10. A method according to claim 9 wherein the compound or salt is incorporated in the range of 0.1 to 10,000 parts per million.

11. A method of controlling a microorganism, bacteria, algae, fungi, and nematode which comprises contacting with said organisms a composition as defined in claim 5 in an amount which is effective to control said organisms.

12. A process for preparing a compound according to claim 1 which comprises contacting at least three mole equivalents of a halogenating agent selected from chlorine, bromine, sulfuryl chloride, sulfuryl bromide, N-chlorosuccinimide, N-bromosuccinimide with a disulfideimidate of the formula

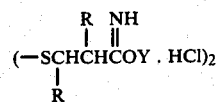

wherein R and R' are hydrogen, halogen, or a ($C_1$–$C_4$)alkyl group, and Y is as defined in claim 1 at temperatures from about 0° C. to 60° C. in an inert non-aqueous solvent.